United States Patent [19]

Ayyangar et al.

[11] Patent Number: 4,764,615
[45] Date of Patent: Aug. 16, 1988

[54] PROCESS FOR THE PREPARATION OF CODEINE FROM MORPHINE

[75] Inventors: Nagaraj R. Ayyangar; Anil R. Choudhary; Uttam R. Kalkote; Vasant K. Sharma, all of Maharashtra, India

[73] Assignee: Council of Scientific & Industrial Research, New Delhi, India

[21] Appl. No.: 940,517

[22] Filed: Dec. 10, 1986

[51] Int. Cl.$^4$ .......................................... C07D 489/02
[52] U.S. Cl. ..................................................... 546/44
[58] Field of Search ......................................... 546/44

[56] References Cited

FOREIGN PATENT DOCUMENTS 0247180  5/1912  Fed. Rep. of Germany ........ 546/44

OTHER PUBLICATIONS

Shaposhnikov, Chemical Abstracts, vol. 31:8833[6] (1937).
Heumann, Chemical Abstracts, vol. 53:4649h (1959).
Kesselring, et al., Chemical Abstracts, vol. 54:3485e (1960).
Stanev, et al., Chemical Abstracts, vol. 55:7460f (1961).

*Primary Examiner*—Donald G. Daus
*Assistant Examiner*—Diana G. Rivers
*Attorney, Agent, or Firm*—Ladas & Parry

[57] ABSTRACT

Codeine is prepared by reacting morphine with trimethyl phenyl ammonium chloride in the presence of an alkali metal carbonate and a hydrocarbon solvent at a temperature of from 40° to 120° C. Codeine is recovered from the reaction mixture. Codeine is useful as an analgesic and antitussive drug.

7 Claims, No Drawings

PROCESS FOR THE PREPARATION OF CODEINE FROM MORPHINE

This invention relates to an improved process for the preparation of codeine from morphine.

Codeine is useful as an analgesic and antitussive drug. Codeine is a methylether of morphine. It occurs naturally in opium to the extent of 2 to 4% depending on the source. Codeine is being prepared synthetically from morphine by methylation of phenolic hyroxyl group because the demand for codeine has far exceeded the quantities that are naturally available from opium.

It is hitherto been known to prepare codeine by the reaction of morphine with the methylating agent such as dimethyl sulphate or methyl chloride or trimethylphenylammonium ethoxide or trimethylphenylammonium hydroxide in presence of a base such as aqueous sodium hydroxide or alcoholic sodium ethoxide. In this connection following references are made. Rodinov, *Bull. Soc. Chim;* 39, 305-25 (1926); 45 109-21 (1928); Schwyze *Bull. Soc. Chim;* 45, 388-92 (1928); Rodinov and Small, *Bull. Soc. Chim;* 45, 188-89 (1928); M. A. Phillips, *Chemists and Druggist,* 183, 661 (1965); J. Kesselring and H. Loffer, *Ger Pat.,* 15069 and 15070 (1958); CA 54 485 (1960); S. Stanev and W. Kamedulsk, *Farmatsiya* (Sofia), 10, 30-5 (1960); CA 55 74605 (1961); W. R. Henmann, *Bull. Narcotics,* U.N. Dept of social affairs, 10, 15-17 (1958); I. Kostantin, *Acta. Pharma,* Iugasolav, 23(3), 169-71 (1973).

The prior art processes disclosed in the above publications involve the use of highly pure morphine (95%) which is obtained from opium. Preparation of pure morphine from opium is a very difficult and lengthy process involving a number of steps. In the above referred known processes leading to the production of codeine, morphine is methylated under highly basic conditions which involves use of aqueous sodium hydroxide or sodium ethoxide as base. This results in the formation of a number of side products. These processes also involve handling of hazardous chemicals such as sodium metal or sodium ethoxide. These processes also make use of an expensive chemical such as absolute alcohol. Furthermore, the yield of the product obtained by the above referred processes is not high since the starting material is lost during the process and besides the starting material being very expensive there is a consequent escalation in the cost of making the final product.

The main disadvantage of these known processes is the use of very costly raw material.

Another disadvantage is the very cumbersome and lengthy process involved in the preparation of pure morphine from opium.

A further disadvantage is the use of pure morphine (95%) in producing codeine.

Yet a further disadvantage is the use of the hazardous nature of chemicals such as sodium metal or sodium ethoxide.

Yet a further disadvantage is the use of costly absolute alcohol.

A further disadvantage is the low yield of codeine.

All the aforesaid disadvantages have been overcome by the process according to the invention which not only utilizes easily accessible and cheap raw materials but also gives a high yield of codeine under mild reaction conditions.

The process of the present invention uses as starting materials, basic chemicals such as anhydrous alkalimetal carbonate, trimethylphenylammonium chloride and morphine. This process envisages the use of morphine having a purity from 30 to 90%.

The main object of the invention is to produce codeine in high yields.

Another object of the invention is to produce codeine by a simple process nder mild reaction conditions.

A further object of the invention is the use of easily accessible cheap raw materials.

Yet a further object of the invention is to use morphine of a purity of 30 to 95%.

Yet a further object of the invention is to produce codeine of high purity directly without any additional purification steps.

Accordingly, the present invention provides a process for the preparation of codeine which comprises reacting morphine with trimethyl phenyl ammonium chloride in the presence of an alkali metal carbonate and a hydrocarbon solvent at a temperature of from 45° to 120° C. and recovering codeine from the reaction mixture.

The trimethyl phenyl ammonium chloride acts as a methylating agent and phase transfer catalyst.

The solvent employed in the process may be xylene or toluence. The heating may be done for a period of 2 to 8 hours, preferably 2-5 hours. After the completion of the reaction the mixture may be cooled to 40° C. The mixture may be distilled to remove the solvents, the filtrate is acidified, steam distilled and basified by known methods.

Morphine of very low purity of 30 to 95% containing gums and resins can be directly used for the reaction. The mixture of morphine and codeine obtained from the natural opium can be utilised in the process of the invention. The yield of codeine is high and therefore minimises the cost of its production. The alkalimetal carbonate employed in the process of the present invention may be selected from sodium or potassium carbonate.

Codeine can be converted to codeine phosphate or codeine sulphate as per the requirement for use as an analgesic/antitussive drug by known methods.

The invention is further illustrated by the following examples; which should not however considered to limit the scope of the invention.

EXAMPLE 1

Morphine of 89.0% purity 320 parts (1 mole part), potassium carbonate 552 parts (4 moles part) and trimethylphenyl-ammonium chloride 188 parts (1.1 moles part) are heated under stirring in toluene (4000 parts) at 45 to 120° C. for 2-5 hrs. The reaction mixture is filtered and toluene is distilled off. The residue is acidified (pH 5 to 5.5) and steam distilled to remove dimethylaniline (120 parts). On basification the product codeine is separated (296 parts, 0.99% yield. mp. 155°-6° C. The purity of codeine is 99% by HPLC. (High presence liquid chromatography).

EXAMPLE 2

Morphine of 89.0% purity 320 parts (1 mole part, potassium carbonate 552 parts (4 moles part) and trimethylphenyl-ammonium chloride 188 parts (1.1 moles part) are heated under strring in xylene (400 parts at 45° to 120° c. for 2-5 hrs. The reaction mixture is filtered and xylene is distilled off. The residue, after removal of xylene, is acidified (pH 5 to 5.5) and steam distilled to remove the dimethylaniline (120 parts). On basification the product codeine is separated in 99% yield. mp. 155°–6° C. The purity of codeine is 99% by HPLC.

EXAMPLE 3

Morphine of 70% purity 407 parts (1 mole part), potassium carbonate 552 parts (4 moles part) and trimethylphenyl-ammonium chloride 188 parts (1.1 moles part) are heated under stirring in toluene (4000 parts) at 45° to 120° C. for 2–5 hrs. to yield 296 parts codeine (99% yield), after workup as in Example 1.

EXAMPLE 4

Morphine of 89.0% purity 320 parts (1 mole part), potassium carbonate 552 parts (4 moles part), water 65 parts and trimethylphenylammonium chloride 188 parts (1.1 moles part) are heated under stirring in toluene (4000 parts) at 45° to 120° C. for 2 to 8 hrs. to yield 296 parts codeine (95.6% yield after workup as in Example 1.

EXAMPLE 5

Morphine of purity 35% 815 parts (1 mole parts), potassium carbonate 552 parts (4 moles part) and trimethylphenyl-ammonium chloride 188 parts (1.1 moles part) are heated under stirring in toluene (5000 parts) at 45° to 120° C. for 2 to 5 hrs. to yield 296 parts codeine (99% yield), after workup as in Example 1.

EXAMPLE 6

Morphine of 89% purity 320 parts (1 mole part), potassium carbonate 414 parts (3 moles part) and trimethylphenyl-ammonium chloride 188 parts (1.1 moles part) are heated under stirring in toluene (4000 parts) at 45°–110° C. for 3–8 hrs. to yield 293 parts of codeine (98.0% yield), after workup as in Example 1.

EXAMPLE 7

Morphine of 82.5% purity, 235 parts (1 mole parts), potassium carbonate 276 parts (2 moles part) and trimethylphenyl-ammonium chloride 188 parts (1.1 moles part) are heated under stirring in toluene at 45°–110° C. for 4–8 hrs. to yield 292 parts of codeine (97.6% yield) after workup as in Example 1.

We claim:

1. An improved process for the preparation of codeine which comprises reacting morphine with trimethyl phenyl ammonium chloride in the presence of an alkali metal carbonate and a hydrocarbon solvent at a temperature of from 45° to 120° C. and recovering codeine from the reaction mixture.

2. A process as claimed in claim 1 wherein the morphine is obtained from natural opium.

3. A process as claimed in claim 1 wherein the morphine has a purity from 30 to 95%.

4. A process as claimed in claim 1 wherein the alkali metal carbonate is selected from sodium carbonate and potassium carbonate.

5. A process as claimed in claim 1 wherein the hydrocarbon solvent is selected from xylene and toluene.

6. A process as claimed in claim 1 wherein he reaction is carried out for a period of 2 to 8 hours.

7. A process as claimed in claim 1 wherein the reaction is carried out for a period of 2 to 5 hours.

* * * * *